United States Patent
Blank et al.

[11] Patent Number: 5,630,800
[45] Date of Patent: May 20, 1997

[54] INJECTION SYRINGE FOR THE MISSING AND APPLICATION OF INJECTION SUBSTANCES

[75] Inventors: Norbert Blank, Strande; Joachim Zwick, Kiel, both of Germany

[73] Assignee: Ferring Arzneimettel GmbH, Kiel, Germany

[21] Appl. No.: 330,935

[22] Filed: Oct. 28, 1994

[30] Foreign Application Priority Data

Nov. 8, 1993 [DE] Germany .................. 43 38 553.2

[51] Int. Cl.$^6$ ................................. A61M 37/00
[52] U.S. Cl. ................ 604/82; 604/89; 604/90; 604/228
[58] Field of Search ............... 604/82–92, 191, 604/228, 218, 187, 220–223, 225, 226, 229, 234, 235, 236, 237, 238, 246

[56] References Cited

U.S. PATENT DOCUMENTS

| | | | |
|---|---|---|---|
| 3,370,754 | 2/1968 | Cook et al. | 604/90 X |
| 3,659,749 | 5/1972 | Schwartz | 604/87 X |
| 3,682,174 | 8/1972 | Cohen | 604/90 |
| 3,749,084 | 7/1973 | Cucchiara | 604/191 X |
| 4,055,177 | 10/1977 | Cohen | 604/90 X |
| 4,116,240 | 9/1978 | Guiney | 604/191 X |
| 4,496,344 | 1/1985 | Kamstra | 604/90 |
| 5,122,117 | 6/1992 | Haber et al. | 604/90 |
| 5,298,024 | 3/1994 | Richmond | 604/90 |
| 5,352,203 | 10/1994 | Vallelunga et al. | 604/110 |
| 5,411,489 | 5/1995 | Pagay et al. | 604/218 |

FOREIGN PATENT DOCUMENTS

| | | |
|---|---|---|
| WO84/00011 | 1/1984 | European Pat. Off. . |
| 0188981 | 7/1986 | European Pat. Off. . |
| 1961166 | 12/1969 | Germany . |
| 124863 | 4/1928 | Switzerland . |
| 1214053 | 12/1970 | United Kingdom . |
| 2229374 | 9/1990 | United Kingdom ........ 604/191 |

*Primary Examiner*—V. Millin
*Assistant Examiner*—V. Alexander
*Attorney, Agent, or Firm*—Nixon & Vanderhye

[57] ABSTRACT

The invention relates to an injection syringe for mixing and applying injection substances having a syringe cylinder and a plunger displaceable therein. The plunger has a stopper at its distal end tightly engaged against the inner surface of the cylinder to form an injection volume in the syringe cylinder. A mixing plunger is displaceable in longitudinal direction and guided through the plunger. The mixing plunger projects from the stopper at its proximal end and, at its distal end, has a mixing piston with at least one opening, passing through the surface of the piston. Injection substances can pass through the one opening when the mixing piston is displaced in the injection volume. An effective thorough mixing of the injection substances takes place through to-and-fro movement of the mixing piston in the injection volume. The invention is applicable both to single injection syringes and to double-chamber syringes to provide better miscibility of solutions, suspensions, etc, with minimal losses of active ingredients.

4 Claims, 4 Drawing Sheets

5,630,800

INJECTION SYRINGE FOR THE MIXING AND APPLICATION OF INJECTION SUBSTANCES

TECHNICAL FIELD

The invention relates to an injection syringe for the mixing and application of injection substances, the injection syringe having a syringe cylinder and a plunger displaceable therein which projects with its proximal end from the cylinder and lies at its distal end with a stopper tightly against the inner surface of the cylinder, in order to form an injection volume in the syringe cylinder.

BACKGROUND

In many cases, injection substances must be brought together and thoroughly mixed before they are used, or specific solutions are to be formed. Examples are aqueous solutions, aqueous suspensions, O/W, W/O emulsions, solutions with soluble dry substances, oily solutions, oily suspensions, solutions with macrocrystals and compresses. Injection substances of the above type are brought together and mixed or dissolved immediately before they are used. In the simplest case, this is performed by placing the substances to be mixed in a small vessel and mixing or dissolving them, e.g., by shaking, whereby the thoroughly mixed injection substance may be drawn up into an injection syringe. This combination of an external vessel for the mixing of the injection substance and an injection syringe is also called a vial syringe. It is clear that, when injection substances of the above type are mixed and drawn up employing a combination of an external vessel and an injection syringe, high losses of one or more active ingredients may occur, as the injection substance placed in the vessel can never be completely taken up into the injection syringe. Moreover, the mixing and drawing up of an injection substance with the vial syringe requires some manual skills on the part of doctors and medical personnel.

Another system for the mixing and application of injection substances of the type mentioned consists of two normal injection syringes whose cannulae or cannula attachments are connected to each other by an attachable line. With this two-syringe system, the filled syringes are connected to each other by means of a connector and the plungers of the two syringes are operated in opposite directions, so that the substances are pumped to and fro between the two syringes. The reduction in cross-section which is caused by the cannula attachments or by the connection line in the connector compared with the syringe cylinders has a substantial throttling effect during the pumping process, the result of which is major turbulences in the flow and thereby a thorough mixing of the substances. However, it is also a drawback with this system that losses of an active ingredient always occur, as injection substance is always left in the syringe which is not used for the application and in the connecting line. In the case of expensive active ingredients, the losses caused thereby are substantial.

The so-called double-chamber syringe, in which the substances to be mixed are contained from the outset in two chambers of the syringe, functions in a similar way. The double-chamber syringe, like a single syringe, contains a plunger with a stopper at the end and also a second stopper which lies between the first stopper and the cannula attachment in the injection volume and divides the latter into a first chamber (between the cannula attachment and the second stopper) and a second chamber (between the first and second stoppers). When the plunger is pressed down, the second stopper is also moved hydraulically, as it were, via the first stopper by the suspension agent present in the second chamber, until it reaches a zone of the syringe cylinder in which the latter has a wider section (bypass) through which the suspension agent passes around the second stopper and overflows out of the first chamber into the second chamber. The substances thus brought together in the first chamber are then mixed by being shaken and the solution or suspension is thereby produced. However, the thorough mixing by means of shaking is not very effective.

An injection syringe with several chambers lying one behind the other in a cylinder for the administration of various injection agents is known from German Patent DE 730 362. The syringe has a syringe cylinder, a first plunger displaceable therein, which lies at its distal end with a stopper tight against the inner surface of the cylinder, and a displaceable second plunger which is guided and displaceable in longitudinal direction through the first plunger and which is fitted at its distal end with a second stopper, so that a first chamber is formed between the first and second stoppers and a second chamber is formed between the second stopper and the bottom of the syringe cylinder which carries the cannula, the two chambers being completely separated from each other by the second stopper. The syringe is also fitted with a bypass line which connects openings in the side wall of the syringe cylinder to the cannula line. The syringe serves to inject an injection agent and, separate therefrom before or after the injection agent, another agent, for example an indifferent solution. In use, the injection agent is drawn up into the first chamber and the solution into the second chamber, with the second stopper being so positioned that it blocks the openings in the cylinder wall to the bypass line. Solution can then be injected first by pressing down the second stopper with the second plunger. As soon as the second stopper has been pushed down a certain distance, it frees the openings in the cylinder wall, as a result of which a link from the first chamber to the cannula is produced through the bypass line. The injection agent can then be injected from the first chamber with the first plunger by pressing down the first stopper with the first plunger. A thorough mixing of the agents in the first and second chambers is not possible with this syringe arrangement.

In EP 0 511 183 A1 there is disclosed a double-chamber syringe with a first chamber with a solvent or suspension agent and a second chamber which contains the substance to be dissolved or suspended. A first stopper, displaceable with a plunger, is arranged in the first chamber and a second displaceable stopper, which separates the two chambers from each other, is arranged in the second chamber. The second displaceable stopper contains a valve element which is raised from its seat by hydrostatic pressure, which is created by advancing the first stopper, and opens a through-flow path from the first into the second chamber. The solvent/suspension agent can be completely forced into the first chamber by advancing the first stopper. There, mixing takes place simply by the uniting of the two agents. The actual injection is carried out when the second stopper is advanced by pressure with the first plunger, in order to thereby drain the first chamber through a cannula. The known double-chamber syringe provides no measures which would make possible an active thorough mixing of the substances which are united in the first chamber.

DISCLOSURE OF THE INVENTION

A primary object of the present invention is to provide an injection syringe for the mixing and application of injection substances which is simply structured and manageable and which achieves a thorough mixing of two or more injection substances.

It is another object to provide a syringe which may be filled with the separate injection substances initially by the manufacturer and may be delivered in this state to hospitals etc., where the separate substances may easily be united and thoroughly mixed before application.

According to the invention a mixing plunger is provided which is guided through the plunger of the syringe and which is displaceable in the longitudinal direction of the cylinder and the respective plungers. The mixing plunger projects with its proximal end from the plunger and is provided at its distal end with a mixing piston which is disposed in the injection volume (the terms proximal and distal are relative to the doctor using the syringe). The mixing piston divides the injection volume defined by the syringe cylinder and by the stopper of the plunger in two part-volumes. The mixing piston is fitted with at least one through opening which forms a connection between the two part volumes of the injection volume. The mixing piston is moved through the injection volume of the syringe cylinder by displacement of the mixing plunger with respect to the plunger which is at rest during the mixing procedure. The movement of the mixing piston through the injection volume causes the injection substances to flow through the at least one opening in the mixing piston, and the passage of the substances through the throttling opening effects an effective mixture.

The invention is applicable to single injection syringes and also to double-chamber syringes, wherein in the latter case the mixing plunger is also guided through the second stopper.

As a result of the inventive configuration of the injection syringe, the mixing process is carried out exclusively in the injection volume of the syringe, as a result of which losses of injection substances are minimized, since no other external lines or vessels are needed in which injection substances could remain behind. As a rule, the syringes and injection substances are made up on the manufacturer's premises by, for example, already introducing a solid (granular or powdery) substance into the injection volume and then supplying this as a syringe/active ingredient combination, in such a way that the doctor or the personnel only need to draw up the solvent or suspension agent. In the case of double-chamber syringes, the solvent is also already supplied as well in one chamber.

The injection syringe according to the invention is also easy to handle since, after the suspension solution which is to be mixed has been drawn up, mixing can be effected easily and effectively by moving the mixing piston to and fro and the syringe can then be used immediately for the injection.

In an advantageous embodiment, the plunger and the stopper are fitted with a central through bore in which the mixing plunger is received and displaceable in a longitudinal direction. The injection volume in the syringe cylinder is sealed off by sealing lips in the through bore lying in a slidable manner against the mixing plunger.

In an advantageous embodiment, the stopper consists of flexible material and is fitted at its outer circumference with circular sealing lips and in the area of the through bore at the inner surface with sealing lips lying in a slidable manner against the mixing plunger.

In another advantageous embodiment, the mixing plunger is fitted with a bulge which is engageable with its corresponding recess in the bore of the plunger or of the stopper. In this way, the mixing plunger can be held secure against movement in a longitudinal direction after the completion of the mixing process.

In another advantageous embodiment, the proximal surface of the mixing piston, which faces the stopper, is designed complementary to the opposite surface of the stopper. The effect of this is that stopper and mixing piston can be brought to lie against each other without the possibility of the injection substance being left behind in an intervening space between them. The bulge and the recess are advantageously arranged in such a way relative to each other that, in the engaged position, the proximal surface of the mixing piston lies tight against the opposite surface of the stopper, with the result that, when the mixing piston is in the engaged position, no intervening space is left between the stopper and the mixing piston.

In another advantageous embodiment, the mixing plunger is made in two pieces in a longitudinal direction with a releasable coupling. As a result, after the mixing of the, injection substances has been carried out by moving the mixing plunger to and fro, that piece of the mixing plunger which projects from the proximal end of the plunger can be removed by releasing the coupling. The injection syringe can then be handled by the user like a normal injection syringe.

In another preferred embodiment, the bottom of the syringe cylinder, which carries the cannula attachment, is shaped in such a way that, when the mixing piston lies against the bottom, there remains a liquid passage from at least one opening in the mixing piston to the cannula attachment. This can be accomplished in a simple manner if the base surface of the mixing piston is level, while the bottom surface of the syringe cylinder, which carries the cannula attachment, extends away or deepens towards the cannula attachment. The effect of this is that, even when the mixing piston lies against the bottom of the syringe cylinder, a liquid passage remains from the at least one opening of the mixing piston to the cannula attachment, so that any injection substance remaining on the other side of the mixing piston can be forced through the opening to the cannula attachment.

In another preferred embodiment, the injection syringe is designed as a double-chamber syringe. A second, freely displaceable stopper, through which the mixing plunger is likewise guided, is provided between the stopper and the mixing piston, so that a chamber for a solvent and suspension agent is formed between the stopper and the second stopper. The second stopper is drawn by pulling out of the mixing plunger until abutment against the stopper, as a result of which the solvent or suspension agent is forced out of the chamber. A line passing through the mixing plunger, whose inlet lies in the chamber for the solvent or suspension agent when the second stopper lies on the mixing piston and whose outlet lies at the distal end of the mixing piston, serves as an outlet for the solvent or suspension agent, in order that the solvent or suspension agent can pass out of the chamber into the part-volume lying between the mixing piston and cannula attachment, in which the substance to be dissolved or suspended is located. When the solvent or suspension agent is fully brought into the said part-volume, the mixing takes place with the help of the mixing plunger as before. The substances to be mixed or dissolved are advantageously already supplied and located in the injection syringe as a syringe/injection agent combination. The line is advantageously fitted with a valve in order that no liquid emerges prematurely, i.e. before the actual use of the syringe, from the chamber for solvent or suspension agent.

In another preferred embodiment according to the present invention, an injection syringe is provided for mixing and applying injection substances, comprising a syringe cylinder and a first plunger displaceable therein and having a proximal end projecting from the cylinder and a stopper at a distal end engaging against an inner surface of the cylinder to form an injection volume in the syringe cylinder, a mixing plunger guided for movement in a longitudinal direction through the first plunger and projecting at a proximal end thereof from the stopper and a mixing piston at the distal end of the mixing plunger and having at least one opening through which injection substances can pass upon displacement of the mixing piston toward the injection volume.

The invention is explained in the following specification with reference to the drawings.

BEST MODE FOR CARRYING OUT THE INVENTION

Figure 1:
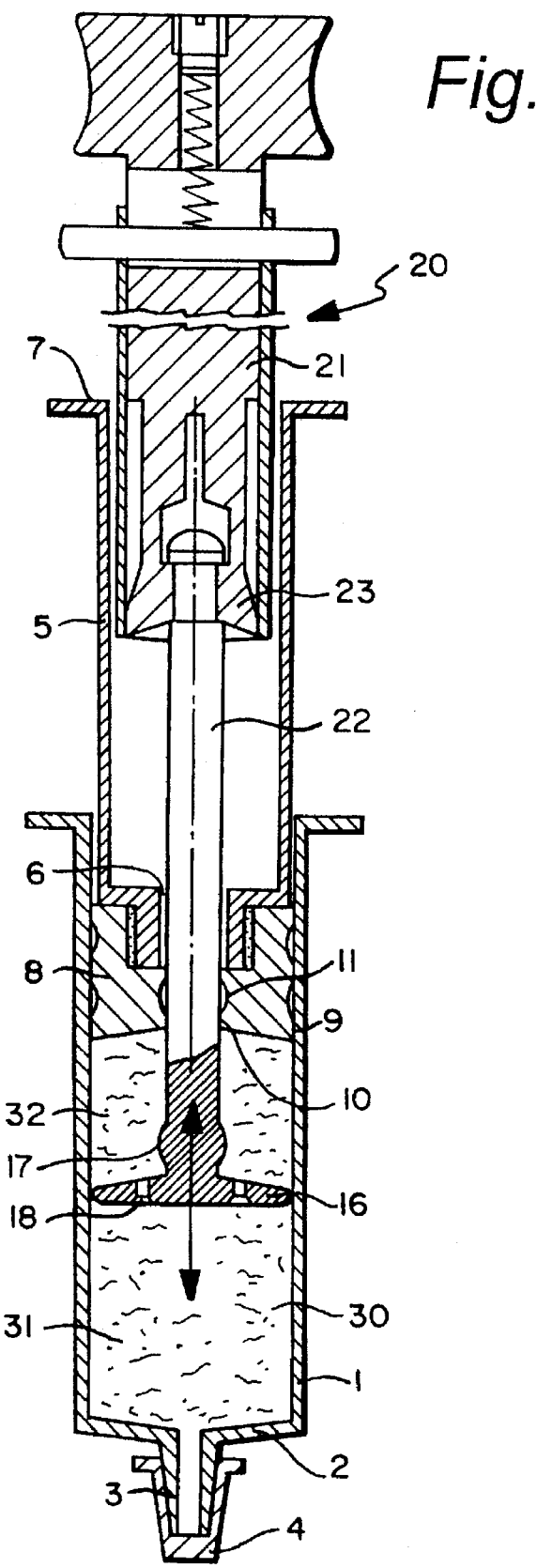
FIG. 1 is a lateral cross-sectional view of an injection syringe according to the invention.

An injection syringe according to the invention as illustrated in FIG. 1, has a syringe cylinder 1 in which a first plunger 5 is displaceably guided. The displaceable plunger 5 is fitted at its end lying in the syringe cylinder 1 with a stopper 8 which lies tight against the inner surface of the syringe cylinder 1. In the embodiment shown, the stopper 8 is made from elastic material, for example rubber, and has three sealing flanges or lips 9 extending about its external circumference. An injection volume 30 is defined by the syringe cylinder 1 and the stopper 8. Arranged centrally at the distal end of the syringe cylinder I is a cannula attachment 3 which can be closed with a cap 4.

The plunger 5 has at its proximal end 7 a flange-like grip, which the user can grasp to pull the injection syringe upwards and against which he can press to apply the substance located in the injection volume 30. The plunger 5 has a central through bore 6 which passes through the stopper 8 to open into the injection volume 30. A displaceable mixing plunger 20 is guided in slidable manner in the through bore 6. The through bore 6 is sealed from the injection volume 30 by inner sealing lips 10 extending about and through the bore of the stopper 8.

The displaceable mixing plunger 20 is fitted at its distal end, lying in the injection volume 30, with a mixing piston 16. The mixing piston 16 lying in the injection volume 30 divides this into a first pad-volume 31 and a second pad-volume 32. The two pad-volumes 31 and 32 are connected to each other by at least one opening 18 formed in the mixing piston 20. The term opening is generally to be understood as meaning any means that allows a liquid stream to pass through or by the mixing piston 16 out of the first part-volume 31 into the second part-volume 32 and vice versa. This can also be achieved, for example, if the outer diameter of the mixing piston 16 is smaller than the inner diameter of the syringe cylinder I or the outer circumference is of oval or star-shaped design or the mixing piston 16 is fitted with inclined bores/inclined slots. In the represented preferred embodiment, the outer circumference of the mixing piston 16 lies however against the inner surface of the syringe cylinder 1, and two through openings 18 are formed through the mixing piston 16.

Figure 2:
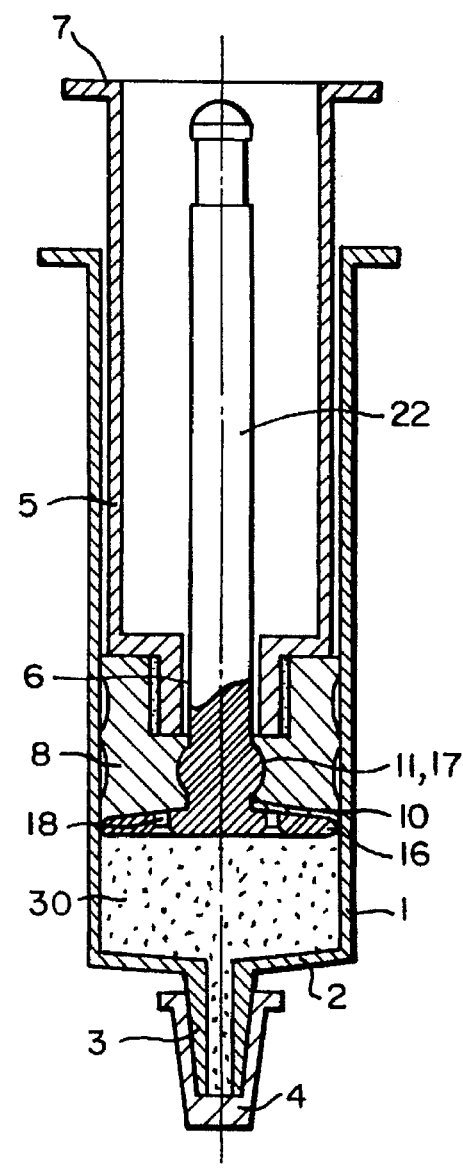
FIG. 2 is a lateral cross-sectional view of the syringe from FIG. 1, wherein the mixing piston is drawn after the mixing process has ended against the stopper.

In use, the injection substances which are to be thoroughly mixed are drawn up as usual into the injection syringe, wherein on delivery the syringe may already contain the substance which is to be dissolved or placed in suspension in its injection volume. This situation is shown in FIG. 2, wherein the substance which is to be dissolved or suspended is located in the injection volume 30 and the syringe is supplied to the user made up as a syringe/active ingredient combination. The solvent or suspension agent then merely needs to be drawn up. The mixing process is then effected, the cannula attachment 3 being closed and the plunger 5 being held secure, by moving the mixing piston 16 to and fro by pushing the mixing plunger 20 to and fro in the injection volume 30. The injection substances which are to be mixed must flow through the opening 18, as the volumes of the first pad-volume 31 and of the second part-volume 32 change constantly with the displacement of the mixing piston. Because of the flow of the injection substances through the opening 18, a thorough-mixing effect occurs, as there results, in the area of the openings, substantially increased flow velocities and appropriate turbulences in the flow which lead to a thorough mixing of the substances.

After the injection substances have been thoroughly mixed by repeated pushing of the mixing plunger 20 to and fro, the injection syringe according to the invention can be used as a normal injection syringe. The mixing plunger 20 is so designed in the preferred embodiment that in the longitudinal direction it consists of two separable parts 21 and 22 which are connected to each other by a coupling 23. After the mixing process has been completed, the proximal part 21 of the mixing plunger 20 can be released by actuation of the coupling 23 and removed. FIG. 2 shows the injection syringe, in which the proximal part 21 (FIG. 1 ) of the mixing plunger 20 is not fitted onto the distal part 22. In this configuration, the syringe is actuated particularly easily by actuation of the plunger 5 at its flange-like grip fitted at the proximal end 7, without the mixing plunger 20 disturbing the application of the injection through the projecting distal part 21.

The mixing plunger 20 is designed near to its distal end in a zone in front of the mixing piston 16 with a bulge or projection 17 which is suitable for engagement with a recess 11 lying between the sealing lips 10 in the through bore of the stopper 8, in order to thus lock the mixing plunger 20 with respect to the plunger 5. This locking of the mixing plunger can be carried out after the thorough mixing of the injection substances has taken place, after which the proximal part 21 of the mixing plunger 20 can be removed by releasing the coupling 23 and the syringe can be used like a normal injection syringe for the application of the thoroughly mixed injection substances. FIG. 2 shows this situation, in which the mixing piston 16 is drawn against the stopper 8 and the distal pad 22 of the mixing plunger 20 is engaged with its bulge 17 in the recess 11 in the through bore of the stopper 8.

In the represented preferred embodiment, the mixing piston 16 is shaped, at its upper side facing the stopper 8, complementary to the latter, wherein the mixing piston 16 is designed with a slightly dropping or tapered surface and the stopper 8 likewise with a slightly dropping or generally complementary tapered surface, with the result that the stopper 8 and the mixing piston 16 can come into close abutment with each other when the mixing plunger 20 is pulled upwards against the plunger 5 or the plunger 5 is forced downwards against the mixing plunger 20. The effect of the complementary shaped surfaces of the stopper 8 and of the mixing piston 16 is that no injection substances can remain behind in any intervening space between the two. The aforementioned engagement of the mixing piston 16 is so designed that the mixing piston 16 lies tight against the stopper 8 in the engaged position.

The syringe cylinder I is fitted, at its end carrying the cannula attachment 3, with a bottom 2 which drops or tapers slightly towards the cannula fitting, while the opposite surface of the mixing piston 16 is level. This configuration ensures that the mixing piston 16 cannot rest tight on the bottom 2 in such a way that a through-flow possibility through the openings 18 to the cannula attachment 3 would be blocked. In this way it is guaranteed that, even if injection substance is still located in the second pad-volume 32 upon application, i.e., the mixing piston 16 is not fully drawn against the stopper 8, injection substances which have remained in the second pad-volume 32 can flow through the opening 18 of the mixing piston 16 to the cannula attachment when the plunger 5 is forced down, with the result that no remnants of injection substances can remain in the second part-volume 32.

Figure 3:
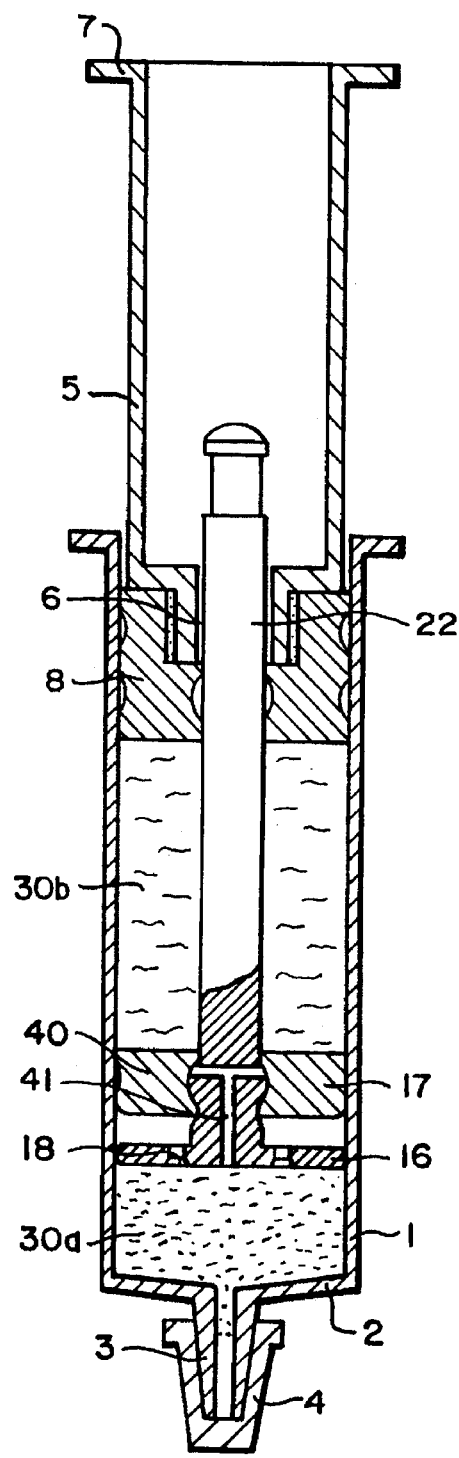
FIG. 3 is a lateral cross-sectional view of one embodiment of the invention for a double-chamber syringe.

In FIG. 3, an injection syringe according to the invention is shown developed as a double-chamber syringe. With this embodiment, a second stopper 40 is provided between the stopper 8 and the mixing piston 16, through which the mixing plunger 20 is guided with its distal part 22. A chamber 30b for a solvent or suspension agent is formed between the first stopper 8 and the second stopper 40, while a chamber 30a for substances to be dissolved or suspended (e.g. powdery substances, microcapsules, etc.) lies between the second stopper 40 and the bottom 2 of the syringe cylinder. The double-chamber syringe can advantageously be made up with a solvent or suspension agent in chamber 30b and with the active ingredient which is to be dissolved in chamber 30a and supplied in this combination. For use, the proximal part 21 (see FIG. 1 ) of the mixing plunger 20 is then fitted onto the distal part 22 and the mixing plunger 20 is then pulled out in the direction out of the syringe cylinder, while the plunger 5 is simultaneously held fast. As a result, sufficient pressure builds up in the chamber 30b with the solvent or suspension agent, so that the second stopper 40 releases itself from the locking at the bulge 17 of the mixing plunger, whereby the lateral openings of the line 41 open to the chamber 30b and the solvent or suspension agent passes out of the chamber 30b through the line 41 into the chamber 30a, and is there brought together with the substance which is to be dissolved. When, as a result of the drawing out of the mixing plunger, all of the solvent or suspension agent has passed out of the chamber 30b into the chamber 30a, the mixing process can be effected there by moving the mixing plunger to and fro as described above.

Figure 4:
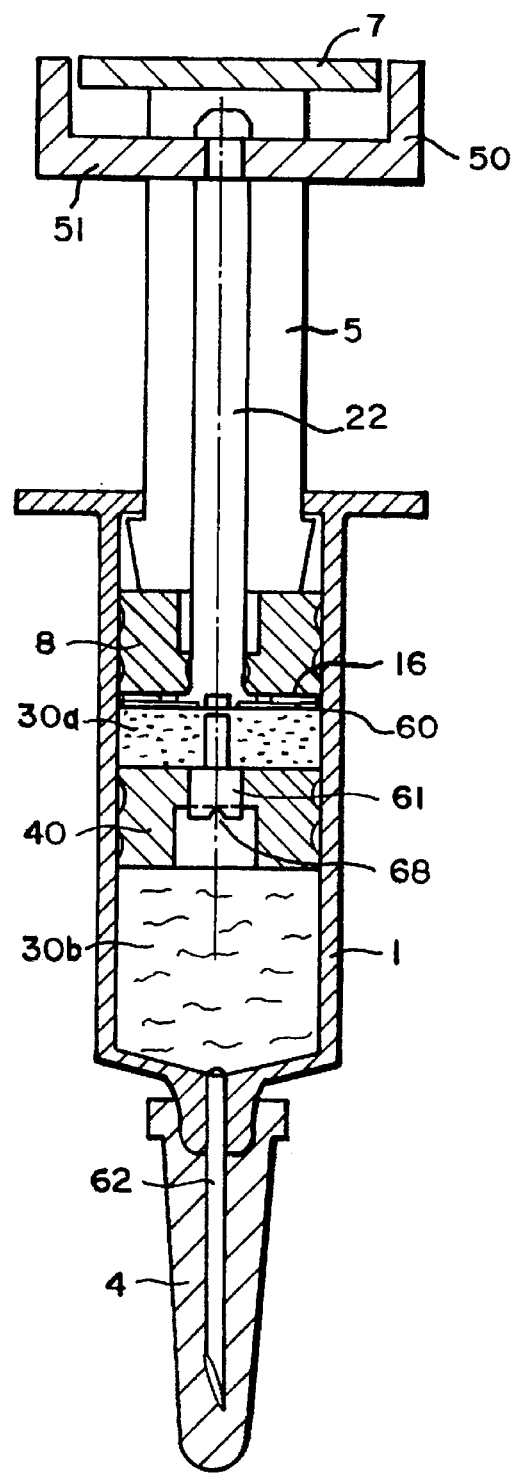
FIG. 4 is a lateral cross-sectional view of an alternative embodiment for a double-chamber syringe.
Figure 4A:
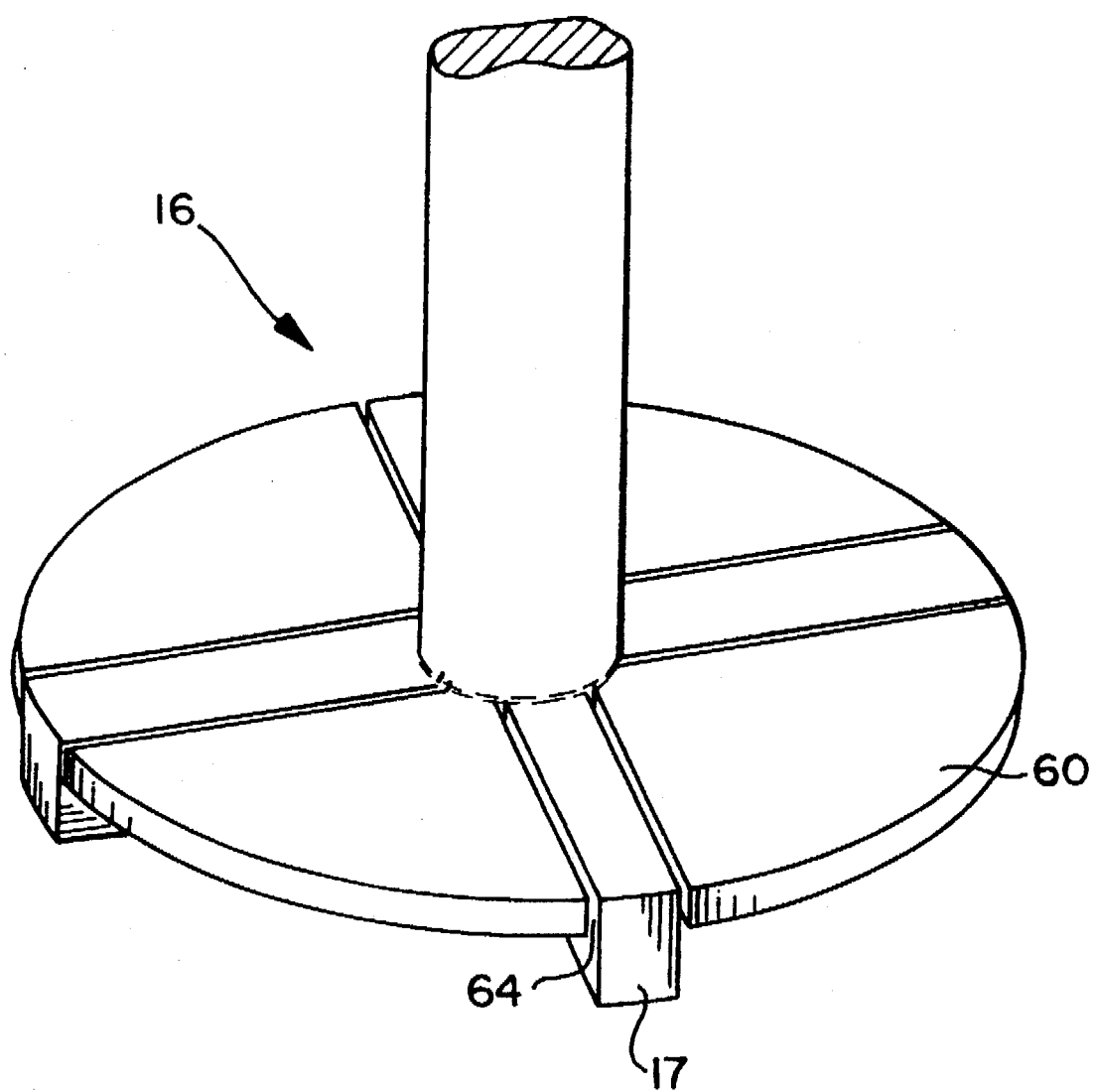
FIG. 4a is a perspective detailed view of the mixing piston of the embodiment according to FIG. 4.
Figure 5:
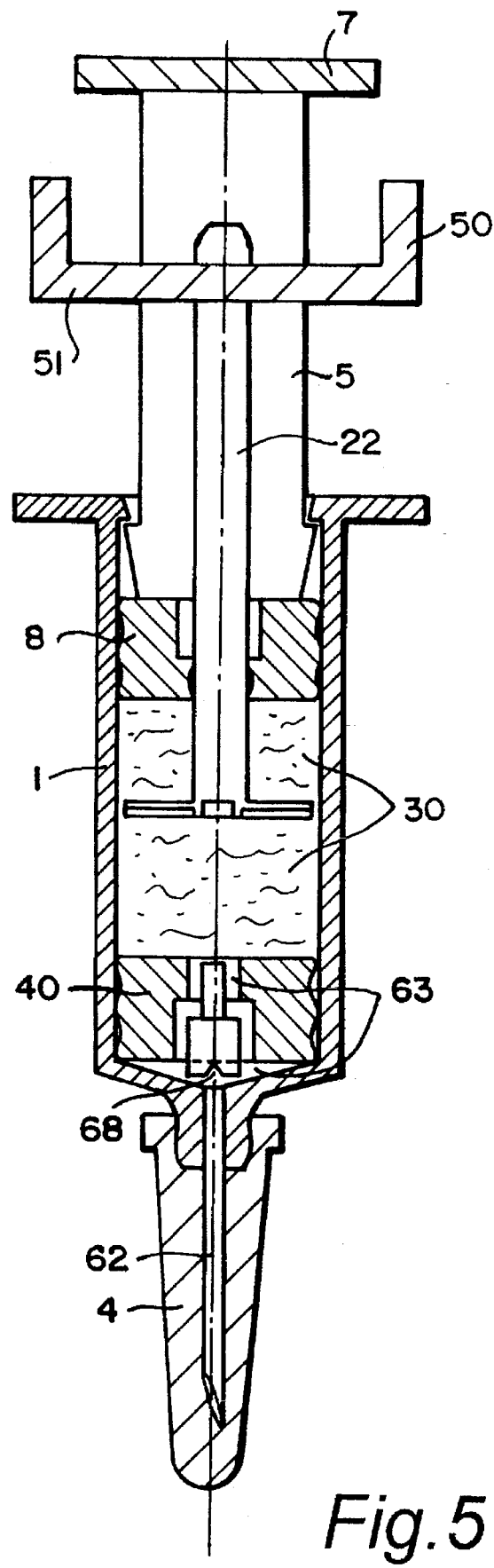
FIG. 5 is a cross-sectional view of the embodiment according to FIG. 4 in a later use phase during thorough mixing.

Another embodiment of an injection syringe developed as a double-chamber syringe is shown in FIGS. 4, 4a and 5. FIG. 4 shows the syringe in a prepared state with substance to be dissolved/suspended and solvent/suspension agent, wherein the syringe is already prepared in this manner on the manufacturer's premises and can be supplied to the user in such a way. In this embodiment, the chamber 30a for the substance to be dissolved or suspended lies in the upper part, while the chamber 30b with solvent or suspension agent lies in that part of the injection volume which faces the cannula 62. In the situation shown in FIG. 4, the chambers 30a and 30b are separated from each other by the second stopper 40 which sits displaceable in the injection volume of the syringe cylinder 1. The second stopper 40 has a bore into which a tapered pin 61 is inserted which forms a tight seal. The tapered pin 61 can be pushed forward, by pressure on its end facing away from the cannula 62, out of the seat in the bore of the second stopper 41.

The configuration of the mixing chamber piston 16 is to be best recognized in FIG. 4a. The openings passing through the surface of the piston are in this case developed as slots 64, wherein a pair of slots defines a land 17 between them. A plurality of such pairs of slots can be provided, for example for pairs of slots, with the result that four lands 17 are formed in a cross-like arrangement. Flexible zones 60, reduced in their thickness, are provided between neighboring lands 17. The material of the piston 16, preferably a plastic material, and the thickness of the flexible zones 60 are selected in such a way that the flexible zones 60 can bend upwards if pressure is exerted on material lying underneath.

In order to put the syringe shown in FIG. 4 into use it is operated as follows. The user moves the mixing plunger 22 by grasping a handle 50, projecting externally over the plunger 5, which comprises for example an external ring which is connected to the mixing plunger by struts 51, wherein the struts are guided through slots in the plunger 5. The handle 50 and thus the mixing plunger 22 are pressed downwards. As a result, the mixing piston 16 is pushed downwards into the chamber 30a with the substance which is to be dissolved, whereby the flexible zones 60 (see FIG. 4a) avoid the counter-pressure through the substance to be dissolved, by bending upwards. As a result, the mixing piston can approach the second stopper 40, which sits relatively firmly in the syringe cylinder 1, and come to lie against a projection of the tapered pin 61. Through further pressure, the mixing piston 16 lying against the projection of the tapered pin 61 releases the tapered pin 61 downwards out of its seat in the stopper 40. The said projection of the tapered pin is laterally flattened on two sides. After the displacement, two flow channels thus form in the stopper 40, with the result that a liquid connection is produced between the chambers 30a and 30b through the bore of the stopper 40. Liquid can then pass out of the chamber 30b through the bore in the stopper 40 and the slot 64 in the mixing piston 16 into the chamber 30a. In this way, the stopper 40 can be forced down with the help of the mixing plunger 22 to that end of the syringe cylinder 1 which lies at the side of the cannula 62.

The said depressed position of the stopper 40 is shown in FIG. 5. In this position, a good thorough mixing can be effected as in the previous embodiments, by moving the mixing piston 16 to and fro by to-and-fro movements of the mixing plunger 22, as a result of which the substance which is to be dissolved is well mixed with the solvent upon passing through the slots 64.

The tapered pin is developed in such a way at its side facing the bottom surface 2 of the syringe cylinder 1 that, when lying against the bottom surface 2, it frees a through-flow path into the cannula 62. This can happen, e.g., if grooves 68 are provided at the side of the tapered pin 61 facing the bottom surface 2.

Instead of the tapered pin 61 seated in the stopper 40, any kind of valve means can be used which is suitable for freeing a throughflow connection 63 through the stopper 40 through the action of force by the mixing piston 16. Such other valve means which are to be opened by mechanical action of the mixing piston 16 may comprise, e.g., a thin layer of material which seals a bore in the second stopper 40 and can be opened by a mandrel or any other means at the mixing piston 16, in order thereby to create a throughflow path through the second stopper 40.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

We claim:

1. A double chamber injection syringe for mixing and applying injection substances, comprising:

a syringe cylinder;

a first plunger displaceable therein and having a proximal end projecting from the cylinder and a stopper at a distal end engaging against an inner surface of said cylinder to form an injection volume in the syringe cylinder;

a mixing plunger guided for movement in a longitudinal direction through said first plunger and projecting at a proximal end thereof from said stopper, said mixing plunger being provided at its distal end with a mixing piston having at least one opening through which injection substances can pass upon displacement of said mixing piston toward the injection volume; and a displaceable second stopper disposed between said mixing piston and one end of said syringe cylinder and separating a first chamber and a second chamber on opposite sides of said second stopper, said first chamber containing a substance to be dissolved or suspended, said second chamber containing a solvent or suspension agent, wherein said second stopper carries a valve responsive to advance of said mixing piston relative to said second stopper to provide communication between said chambers within the syringe cylinder, to enable transfer of said solvent or suspension agent to the first chamber by downward displacement of the second stopper in response to depression of the mixing piston.

2. An injection syringe according to claim 1, wherein said valve includes a tapered pin seated in a bore of said second stopper, said pin being responsive to pressure exerted on an end face thereof facing said mixing piston for release from its seat in the bore of the stopper.

3. An injection syringe according to claim 1, including a tapered pin carried by said second stopper and having along its side facing a bottom surface of the syringe cylinder, at least one groove for maintaining a through-flow path between the bottom surface and the tapered pin.

4. An injection syringe according to claim 1, wherein the mixing piston has flexible zones for flexing in response to a pressure perpendicular to the surface of the mixing piston.

* * * * *